US008865843B2

(12) United States Patent
Saliya et al.

(10) Patent No.: US 8,865,843 B2
(45) Date of Patent: Oct. 21, 2014

(54) FLUORINATED SAG CONTROL AGENT AND USE THEREOF

(75) Inventors: Rajesh Gopalan Saliya, Philadelphia, PA (US); Ayumu Yokoyama, Wallingford, PA (US); Sheau-Hwa Ma, West Chester, PA (US); Axel Hans-Joachim Herzog, West Chester, PA (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 57 days.

(21) Appl. No.: 13/496,224

(22) PCT Filed: Sep. 16, 2010

(86) PCT No.: PCT/US2010/049127
§ 371 (c)(1),
(2), (4) Date: Mar. 15, 2012

(87) PCT Pub. No.: WO2011/037818
PCT Pub. Date: Mar. 31, 2011

(65) Prior Publication Data
US 2012/0171478 A1 Jul. 5, 2012

Related U.S. Application Data

(60) Provisional application No. 61/246,163, filed on Sep. 28, 2009.

(51) Int. Cl.
*C08G 18/00* (2006.01)
*C08G 18/28* (2006.01)
*C08G 75/00* (2006.01)
*B05D 3/00* (2006.01)

(52) U.S. Cl.
USPC .............. 525/452; 525/459; 528/69; 528/70; 528/373; 528/391; 528/401; 427/385.5

(58) Field of Classification Search
USPC .......... 525/459, 540, 452; 528/44, 69, 70, 78, 528/367, 373, 391, 401; 427/372.2, 385.5
See application file for complete search history.

(56) References Cited

U.S. PATENT DOCUMENTS

| 3,893,956 A | 7/1975 | Brandt |
| 4,311,622 A | 1/1982 | Buter |
| 4,528,319 A | 7/1985 | Ottaviani et al. |
| 4,677,028 A | 6/1987 | Heeringa et al. |
| 4,851,294 A | 7/1989 | Buter |
| 5,098,983 A | 3/1992 | Mosbach et al. |
| 5,334,637 A | 8/1994 | Zwiener et al. |
| 5,473,011 A | 12/1995 | Laas et al. |
| 5,633,362 A | 5/1997 | Nagarajan et al. |
| 5,686,276 A | 11/1997 | Laffend et al. |
| 5,821,092 A | 10/1998 | Nagarajan et al. |
| 6,221,494 B1 | 4/2001 | Barsotti et al. |
| 6,479,612 B1 | 11/2002 | Del Pesco et al. |
| 6,720,384 B1 | 4/2004 | Mayer et al. |
| 6,730,807 B1 | 5/2004 | Haeberle et al. |
| 6,767,958 B2 | 7/2004 | Laas et al. |
| 7,169,475 B2 | 1/2007 | Sormani et al. |
| 2002/0076501 A1 | 6/2002 | Costantini et al. |
| 2004/0258923 A1* | 12/2004 | Sormani et al. ............ 428/422.8 |
| 2006/0186368 A1* | 8/2006 | Liu et al. ...................... 252/8.57 |
| 2006/0188729 A1* | 8/2006 | Schubert et al. ........... 428/423.1 |
| 2006/0270782 A1 | 11/2006 | Huybrechts et al. |
| 2007/0066785 A1* | 3/2007 | Acosta et al. .................... 528/44 |
| 2008/0132638 A1 | 6/2008 | Huybrechts et al. |
| 2008/0132639 A1 | 6/2008 | Huybrechts et al. |
| 2008/0188606 A1 | 8/2008 | Asada et al. |
| 2009/0143608 A1* | 6/2009 | Herzog et al. ................ 558/437 |
| 2009/0148654 A1* | 6/2009 | Brown et al. ................... 428/96 |
| 2010/0265580 A1* | 10/2010 | Yun et al. ...................... 359/485 |

FOREIGN PATENT DOCUMENTS

WO 2006088593 A1 8/2006

OTHER PUBLICATIONS

ISA USPTO, International Search Report and Written Opinion for Application No. PCT/US2010/049127, dated Nov. 12, 2010.
ISA USPTO, International Preliminary Report on Patentability for Application No. PCT/US2010/049127, dated Apr. 12, 2012.
Mexican Institute of Industrial Property, Notice of Allowance issued in Application No. MX/a/2012/003537, dated Dec. 4, 2013.
Binkman, E. et al. "Smart rheology resins for coatings," Paint & Coatings Industry, Sep. 2003, [retrieved on Jan. 30, 2014]. Retrieved from Internet: <URL: http://www.highbeam.com/doc/1G1-109265635.html/print.
Bosma, M. et al. "The role of sag control agents in optimizing the sag/leveling balance and a new powerful tool to study this," Progress in Organic Coatings, 2006, pp. 97-104, vol. 55.
Bosma, M. et al. "Smoother by design," European Coatings Journal, Dec. 2007.

\* cited by examiner

*Primary Examiner* — Thao T. Tran
(74) *Attorney, Agent, or Firm* — Ingrassia Fisher & Lorenz, P.C.

(57) ABSTRACT

The present disclosure is directed to a sag control agent comprising a reaction product of an isocyanate and a fluorinated amine. This disclosure is further directed to a coating composition comprising the sag control agent. This disclosure is also directed to a process of forming a sag-free coating layer on a substrate.

23 Claims, No Drawings

FLUORINATED SAG CONTROL AGENT AND USE THEREOF

CROSS-REFERENCE TO RELATED APPLICATION

This application claims priority from U.S. Provisional Application Ser. No. 61/246,163 (filed Sep. 28, 2009), the disclosure of which is incorporated by reference herein for all purposes as if fully set forth.

FIELD OF INVENTION

The present invention is directed to a sag control agent comprising a reaction product of an isocyanate and a fluorinated amine. This invention is further directed to a coating composition comprising the sag control agent.

BACKGROUND OF INVENTION

A typical coating finish over a substrate comprises some or all of the following layers: (1) one or more primer layers that provide adhesion and basic protection, and also cover minor surface unevenness of the substrate; (2) one or more colored layers, typically pigmented, that provide most of the protection, durability and color; and (3) one or more clearcoat layers that provide additional durability and improved appearance. A colored topcoat layer can be used in place of the colored layer and clearcoat layer.

In some industrial applications, such as coating metal pipes, trucks, large industrial equipments, and large entertainment equipments, it is often desired to complete the coating process in a short period of time while still achieving good adhesion, protection, durability and appearance. Conventional coating composition typically produces a thin cured dry coating layer that may not have sufficient thickness to cover unevenness of the substrate if only a single layer is used. That could result in undesired appearance. When conventional coatings are applied at a high coating thickness, surface coating defects such as microfoaming, low gloss, and sagging may occur. Thick coating layers are typically prone to sagging defects, especially for coating layers applied on vertical surfaces.

Sag control agent can be used to control sag of coatings, especially when a thick coating layer is desired. Examples of conventional sag control agents are described in U.S. Pat. No. 4,677,028 and U.S. Pat. No. 4,851,294. However, most of them are so called "opaque" sag control agents due to their opalescent appearance in coatings.

Therefore, there is a need for a new sag control agent for further improved sag free coating thickness.

STATEMENT OF INVENTION

This invention is directed to a sag control agent comprising a reaction product of reactants comprising an isocyanate component comprising an isocyanate and an amine component comprising a fluorinated amine.

This invention is further directed to a sag control agent comprising a reaction product of reactants comprising an isocyanate component comprising an isocyanate and an amine component comprising a fluorinated amine having the formula:

$$Rf—X—NH_2 \quad (I)$$

wherein, Rf is a fluorocarbon or perfluorocarbon having 1 to 20 carbon atoms, and X is a connecting di-radical $C_1$ to $C_{20}$ alkyl, $C_6$ to $C_{20}$ aryl, O—$R^1$—S(O)$_k$—$R^{1'}$, $R^1$—S(O)$_k$—$R^{1'}$, $R^1$—$NR^2$—$R^{1'}$, $C_1$ to $C_{20}$ substituted alkyl, $C_6$ to $C_{20}$ substituted aryl, or a combination thereof, k=0, 1 or 2; wherein $R^1$ or $R^{1'}$ is independently $C_1$ to $C_{10}$ alkyl, $C_6$ to $C_{10}$ aryl, $C_1$ to $C_{10}$ substituted alkyl, $C_6$ to $C_{10}$ substituted aryl, or a combination thereof, and wherein $R^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl.

This invention is further directed to a coating composition comprising:
i) a sag control agent comprising a reaction product of reactants comprising an isocyanate component comprising an isocyanate and an amine component comprising a fluorinated amine; and
ii) a polymer binder.

This invention is further directed to a process for forming a sag-free coating layer on a substrate, said process comprising the steps of:
A) applying a coating composition over said substrate forming a sag-free wet coating layer having a wet coating thickness in a range of from 8 to 36 mils, wherein said coating composition comprises:
  i) a sag control agent comprising a reaction product of reactants comprising an isocyanate component comprising an isocyanate and an amine component comprising a fluorinated amine having the formula:

$$Rf—X—NH_2 \quad (I)$$

wherein, Rf is a fluorocarbon or perfluorocarbon having 1 to 20 carbon atoms, and X is a connecting di-radical $C_1$ to $C_{20}$ alkyl, $C_6$ to $C_{20}$ aryl, O—$R^1$—S(O)$_k$—$R^{1'}$, $R^1$—S(O)$_k$—$R^{1'}$, $R^1$—$NR^2$—$R^{1'}$, $C_1$ to $C_{20}$ substituted alkyl, $C_6$ to $C_{20}$ substituted aryl, or a combination thereof, k=0, 1 or 2; wherein $R^1$ or $R^{1'}$ is independently $C_1$ to $C_{10}$ alkyl, $C_6$ to $C_{10}$ aryl, $C_1$ to $C_{10}$ substituted alkyl, $C_6$ to $C_{10}$ substituted aryl, or a combination thereof, and wherein $R^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl; and
  ii) a polymer binder; and
B) curing said sag-free wet coating layer to form said sag-free coating layer.

DETAILED DESCRIPTION

The features and advantages of the present invention will be more readily understood, by those of ordinary skill in the art, from reading the following detailed description; It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

"Gloss" means surface gloss of a coating surface and is related to the amount of incident light that is reflected at the specular reflectance angle of the mean of that surface. Gloss can be measured with a specular glossmeter, such as those available from Byk-Gardener, Geretsried, Germany or other locations.

"DOI" (Distinctness of Image) is a quantitative measure of coating appearance that measures the light reflected at and around the specular reflectance angle. It can be determined according to the method described in ASTM D 5767. DOI can be measured with wave scan instruments, such as those available from Byk-Gardener, Geretsried, Germany or other locations. DOI measures not only the amount of incident light that is reflected at the specular reflectance angle, but also the distribution of the reflected light around the reflectance specular angle, typically +/−0.3° from the specular angle. A coating surface that gives fuzzy or distorted image generally produces a low DOI reading. A coating reflecting 100% of lights at the specular angle gives a DOI reading of 100.

The term "sag", "sagging" or "sagging defect" refers to coating defects such as dropping line, sagging curtains, tearing drops, or other defects, irregularities and variations in coating that cause the coating to be un-smooth. The term "sag-free" or "free of sagging" or "free of sag" means a coating that is free of sagging defects.

The term "two-pack coating composition", also known as "2K coating composition", refers to a coating composition having two packages that are stored in separate containers and sealed to increase the shelf life of the coating composition during storage. The two packages are mixed just prior to use to form a pot mix, which has a limited pot life, typically ranging from a few minutes (15 minutes to 45 minutes) to a few hours (4 hours to 8 hours). The pot mix is then applied as a layer of a desired thickness on a substrate surface. After application, the layer dries and cures at ambient or at elevated temperatures to form a coating on the substrate surface having desired coating properties, such as, adhesion, gloss, and DOI.

The term "crosslinkable component" refers to a component having "crosslinkable functional groups" that are functional groups positioned in molecules of the compound, oligomer, polymer, the backbone of the polymer, pendant from the backbone of the polymer, terminally positioned on the backbone of the polymer, or a combination thereof, wherein these functional groups are capable of crosslinking with crosslinking functional groups (during the curing step) to produce a coating in the form of crosslinked structures. One of ordinary skill in the art would recognize that certain crosslinkable functional group combinations would be excluded, since, if present, these combinations would crosslink among themselves (self-crosslink), thereby destroying their ability to crosslink with the crosslinking functional groups. A workable combination of crosslinkable functional groups refers to the combinations of crosslinkable functional groups that can be used in coating applications excluding those combinations that would self-crosslink.

Typical crosslinkable functional groups can include hydroxyl, thiol, isocyanate, thioisocyanate, acetoacetoxy, carboxyl, primary amine, secondary amine, epoxy, anhydride, ketimine, aldimine, or a workable combination thereof. Some other functional groups such as orthoester, orthocarbonate, or cyclic amide that can generate hydroxyl or amine groups once the ring structure is opened can also be suitable as crosslinkable functional groups.

The term "crosslinking component" refers to a component having "crosslinking functional groups" that are functional groups positioned in molecules of the compound, oligomer, polymer, the backbone of the polymer, pendant from the backbone of the polymer, terminally positioned on the backbone of the polymer, or a combination thereof, wherein these functional groups are capable of crosslinking with the crosslinkable functional groups (during the curing step) to produce a coating in the form of crosslinked structures. One of ordinary skill in the art would recognize that certain crosslinking functional group combinations would be excluded, since, if present, these combinations would crosslink among themselves (self-crosslink), thereby destroying their ability to crosslink with the crosslinkable functional groups. A workable combination of crosslinking functional groups refers to the combinations of crosslinking functional groups that can be used in coating applications excluding those combinations that would self-crosslink.

Typical crosslinking functional groups can include hydroxyl, thiol, isocyanate, thioisocyanate, acetoacetoxy, carboxyl, primary amine, secondary amine, epoxy, anhydride, ketimine, aldimine, orthoester, orthocarbonate, cyclic amide or a workable combination thereof.

The term "binder" or "polymer binder" as used herein refers to film forming constituents of a coating composition that typically comprises one or more polymers, such as one or more acrylic polymers, one or more polyester polymers, one or more polyether polymers, one or more oligomers, or a combination thereof. A binder can comprise a crosslinkable component and a crosslinking component in that the crosslinkable component can react with the crosslinking component to form crosslinked structures, such as a coating film or a coating layer. The binder in this disclosure can further comprise other polymers, compounds or molecules that are essential for forming crosslinked coatings having desired properties, such as good adhesion, high DOI and free of sagging at high coating thicknesses. Additional components, such as solvents, pigments, catalysts, rheology modifiers, antioxidants, UV stabilizers and absorbers, leveling agents, antifoaming agents, anti-cratering agents, or other conventional additives are not included in the term. One or more of those additional components can be included in the coating composition of this disclosure.

The term "radiation curable coating" or "radiation curable coating composition" refers to a coating system that can be cured by actinic radiation and can typically comprise polymerizable monomers that have ethylenically unsaturated double bonds, such as acrylic or methacrylic double bonds. Sources of actinic radiation may be natural sunlight or artificial radiation sources. Examples of actinic radiation can include, but not limited to, ultraviolet radiation, such as UV-A, UV-B, UV-C, UV-V radiation, or other radiations having a broad range of wavelengths, which are known to those skilled in the art. Actinic radiation can also include electron-beam radiation, also known as e-beam. A coating curable by any of the aforementioned UV radiations can also be referred to as a UV coating, a UV curable coating or a UV curable coating composition.

The term "mono-cure coating" or "mono-cure coating composition" refers to a coating that can be cured by one curing mechanism. Examples of mono-cure coating can include aforementioned UV curable coating or a coating curable by chemical crosslink such as a coating composition comprising the aforementioned crosslinkable and crosslinking components.

The term "dual-cure coating" or "dual-cure coating composition" refers to a coating that can be cured by two curing mechanisms, such as UV radiation and chemical crosslink. For example, a dual-cure type UV curable coating composition can comprise polymerizable monomers having ethylenically unsaturated double bonds and a crosslinkable component having hydroxyl functional groups. Such dual-cure coating composition can be cured by a combination of UV radiation and a crosslinking component having one or more isocyanates or other crosslinking functional groups.

The term "waterborne coating", "waterborne coating composition", "aqueous coating", or "aqueous coating composition" refers to a paint, a coating composition or a coating system that primarily uses water as a solvent to disperse coating components therein.

The term "solvent borne coating" or "solvent borne coating composition" refers to a coating composition, paint or a coating system that primarily uses organic solvent to disperse coating components therein.

The term "vehicle", "automotive", "automobile" or "automotive vehicle" can include an automobile, such as car, bus, truck, semi truck, pickup truck, SUV (Sports Utility Vehicle); tractor; motorcycle; trailer; ATV (all terrain vehicle); heavy duty mover, such as, bulldozer, mobile crane and earth mover; airplanes; boats; ships; and other modes of transport.

This disclosure is directed to a sag control agent comprising a reaction product of reactants comprising an isocyanate component comprising an isocyanate and an amine component comprising a fluorinated amine.

The fluorinated amine can have the formula:

$$Rf—X—NH_2 \quad (I)$$

wherein, Rf is a fluorocarbon or perfluorocarbon having 1 to 20 carbon atoms, and X is a connecting di-radical $C_1$ to $C_{20}$ alkyl, $C_6$ to $C_{20}$ aryl, $O—R^1—S(O)_k—R^{1'}$, $R^1—S(O)_k—R^{1'}$, $R^1—NR^2—R^{1'}$, $C_1$ to $C_{20}$ substituted alkyl, $C_6$ to $C_{20}$ substituted aryl, or a combination thereof, k=0, 1 or 2; wherein $R^1$ or $R^{1'}$ is independently $C_1$ to $C_{10}$ alkyl, $C_6$ to $C_{10}$ aryl, $C_1$ to $C_{10}$ substituted alkyl, $C_6$ to $C_{10}$ substituted aryl, or a combination thereof, and wherein $R^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl.

X, $R^1$, $R^{1'}$, $R^1$, or $R^2$ can also have one or more fluorine or other halogen atoms, or one or more fluorocarbon or perfluorocarbon groups that can be the same as or different from the Rf, as substitutes for one or more hydrogen atoms.

The Rf can be a $C_1$ to $C_{20}$ fluoroalkyl, a $C_6$ to $C_{20}$ fluoroaryl, a $C_1$ to $C_{20}$ perfluoroalkyl or a $C_6$ to $C_{20}$ perfluoroaryl. It can be preferred that the fluorocarbon or the perfluorocarbon can have 1 to 8 carbon atoms. It can be further preferred that the fluorocarbon or the perfluorocarbon can have 1 to 6 carbon atoms.

It is preferred that the amine group is at least 3 atoms, preferably at least 4 atoms, away from the Rf group. The connecting di-radical X can be a $(CH_2)_m$, $O(CH_2)_m—S(O)_k—(CH_2)_n$, $(CH_2)_m—S(O)_k—(CH_2)_n$, $(CH_2)_m—NR^2—(CH_2)_n$, or substituted $(CH_2)_m$, $O(CH_2)_m—S(O)_k—(CH_2)_n$, $(CH_2)_m—S(O)_k—(CH_2)_n$, or $(CH_2)_m—NR^2—(CH_2)_n$ wherein one or more hydrogen atoms are substituted with a $C_1$ to $C_{10}$ alkyl or $C_1$ to $C_{10}$ substituted alkyl, wherein m and n are independently zero or positive integers, and m+n is in a range of from 3 to 20.

The fluorinated amine can be produced by known processes, such as acid catalyzed deacylation or base catalyzed deacylation as described in U.S. Patent Application No. 2009/0143608, filed on Nov. 18, 2008. Examples of suitable fluorinated amines can include $C_6F_{13}C_2H_4—S—C_2H_4NH_2$, $C_6F_{13}C_2H_4—S(O)—C_2H_4NH_2$, $C_6F_{13}C_2H_4—S(O)_2—C_2H_4NH_2$, and $CF_3(CF_2)_2O(CF_2)_2C_2H_4—S—C_2H_4NH_2$.

The sag control agent can comprise 50% to 100%, weight percent of the total weight of the amine component, of the fluorinated amine. In a further example, the sag control agent can comprise 60% to 100%, weight percent of the total weight of the amine component, of the fluorinated amine. In an even further example, the sag control agent can comprise 70% to 100%, weight percent of the total weight of the amine component, of the fluorinated amine. In yet another example, the sag control agent can comprise 80% to 100%, weight percent of the total weight of the amine component, of the fluorinated amine. In even yet another example, the sag control agent can comprise 90% to 100%, weight percent of the total weight of the amine component, of the fluorinated amine. In one example, the amine component can comprise one or more fluorinated amines selected from the group consisting of $C_6F_{13}C_2H_4—S—C_2H_4NH_2$, $C_6F_{13}C_2H_4—S(O)—C_2H_4NH_2$, $C_6F_{13}C_2H_4—S(O)_2—C_2H_4NH_2$, $CF_3(CF_2)_2O(CF_2)_2C_2H_4—S—C_2H_4NH_2$, and a combination thereof. In another example, the amine component can consist of $C_6F_{13}C_2H_4—S—C_2H_4NH_2$, $C_6F_{13}C_2H_4—S(O)—C_2H_4NH_2$, $C_6F_{13}C_2H_4—S(O)_2—C_2H_4NH_2$, $CF_3(CF_2)_2O(CF_2)_2C_2H_4—S—C_2H_4NH_2$, and a combination thereof.

In addition to the fluorinated amine, the amine component can further comprise one or more non-fluorinated amines. The term "non-fluorinated amine" used herein refers to an aliphatic, cycloaliphatic, or aromatic amine, or a polyamine that is free from any Rf groups. The amine component can comprise a non-fluorinated primary amine, a non-fluorinated secondary amine, or a combination thereof. The amine component can also comprise a non-fluorinated monoamine having one amine group, a non-fluorinated polyamine having 2 or more amine groups, or a combination thereof. Primary amines can be preferred. Examples of non-fluorinated amines can include, but not limited to, benzyl amine, ethylamine, n-propylamine, 2-propylamine, n-butylamine, 2-butylamine, t-butylamine, n-pentylamine, α-methylbutylamine, α-ethylpropylamine, β-ethylbutylamine, hexylamine, octylamine, decylamine, stearylamine, cyclohexylamine, aniline, and hexamethylene diamine. A combination of the non-fluorinated amines can be suitable. Further examples of non-fluorinated amines can include diethylene triamine to pentaethylene hexamine, or dipropylene triamine to pentapropylene hexamine and other aliphatic, cycloaliphatic or aromatic amines or polyamines.

The isocyanate can be a monoisocyanate, a diisocyanate, a trimer of diisocyanate, a polyisocyanate, or a combination thereof. The isocyanate component can comprise one or more isocyanates. In one example, the isocyanate can be a diisocyanate. In another example, the isocyanate can be a combination of a mixture of different isocyanates. In yet another example, the isocyanate can be hexamethylene diisocyanate.

Suitable isocyanate can be mono- or polyisocyanate and can include blocked or un-blocked aliphatic, cycloaliphatic, heterocyclo, or aromatic di-, tri- or multivalent isocyanates. For example, any aliphatic, aralphatic, cycloaliphatic or aromatic polyisocyanate with a functionality of 2.0 to 5.0 can be used. The polyisocyanates usually contain 3 to 40, preferably 4 to 20 carbon atoms. It is preferred to use a symmetrical aliphatic or cycloaliphatic diisocyanate and/or an oligomer of such a diisocyanate. Symmetrical diisocyanates and/or isocyanurate-trimers of symmetrical diisocyanates can be suitable. Examples of suitable diisocyanates can include: tetramethylene-1,4-diisocyanate, hexamethylene-1,6-diisocyanate (HDI) (also known as 1,6-hexamethylene diisocyanate or hexamethylene diisocyanate), dicyclohexyl dimethylmethane-4,4'-diisocyanate, diphenylmethane-4,4'-diisocyanate, cyclohexyl-1,4-diisocyanate, dicyclohexyl methane-4,4'-diisocyanate, 1,5-dimethyl-2,4-di(diisocyanato ethyl) benzene, and 1,3,5-trimethyl-2,4-di(diisocyanato methyl) benzene. Also oligomers of those diisocyanates, e.g., the dimeric and/or trimeric derivatives of the diisocyanates, such as, the uretdione, isocyanurate and biuret analogues can be used. The polyisocyanates can also contain carbodiimide, allophanate, urethane and urea groups. Examples can include oligomers of hexamethylene-1,6-diisocyanate and isocyanurate-trimer of hexamethylene-1,6-diisocyanate. Any of the aforementioned isocyanates can be blocked or unblocked. If a blocked isocyanate is used, it can be deblocked prior to or during the reaction between the isocyanate component and the amine component.

The sag control agent, herein referred to as SCA, can be produced by reacting the isocyanate component and the amine component in the presence or in the absence of one or more polymers. One example for producing the SCA in the absence of polymers can include the use of a polar solvent such as N-methyl pyrrolidone to form an SCA solution. Typically, small amount of a stabilizer or a mixture of stabilizers can be added to the SCA solution. Examples of stabilizers can include inorganic compound such as LiCl, LiBr, NaCl, KCl, CaCl2, LiNO3, LiOC(O)Me or other Li-salts of carboxylic acids, benzoic acids or substituted benzoic acids, with LiCl as the preferred inorganic compound. Such SCA solution can be added directly to a coating composition to achieve the desired rheology or sag control effect. When the SCA is produced in the presence of one or more polymers, the polymers can be the same or different from binder polymers used for the coating composition that the SCA is to be mixed with. The sag control agent can comprise one or more polymers.

The one or more polymers can be one or more acrylic polymers, one or more polyester polymers, one or more polyether polymers, one or more oligomers, or a combination thereof. Typical acrylic polymers, polyester polymers, polyether polymers or oligomers that are suitable for coating compositions can be used. Any of the aforementioned polymers can be straight chain polymers (also known as linear polymers), branched polymers, block copolymers, or graft polymers. The one or more polymers can have functional groups or pendant moieties, such as, for example, hydroxyl, thiol, or carboxyl groups. It is preferred that the functional groups in the one or more polymers have lower reactivity towards the isocyanate groups than that of the amine groups of the fluorinated amine.

The one or more acrylic polymers can include a functional acrylic polymer. In one example, the functional acrylic polymers can be a hydroxyl acrylic polymer.

The one or more polyester polymers can include any polyester polymers suitable for use in coating compositions. The polyester polymers can have functional groups, such as, for example, hydroxyl, thiol, or carboxyl groups and can be linear polymers of branched polymers.

The one or more oligomers can include acrylic oligomers, polyester oligomers, and any other oligomers that are suitable for use in coating compositions. The oligomers can also have one or more of the aforementioned functional groups. In one example, the oligomer can be a hydroxyl oligomer.

The one or more polyether polymers can be any polyether polymers suitable for coatings. In one example, the one or more polyether polymers can comprise a polytrimethylene ether diol having a Mn (number average molecular weight) in a range of from 500 to 10,000 and can be prepared by an acid-catalyzed polycondensation of 1,3-propanediol. A bio-route via fermentation of a renewable resource can be used to obtain the 1,3-propanediol. One example of renewable resources is corn since it is readily available and has a high rate of conversion to 1,3-propanediol and can be genetically modified to improve yields to the 1,3-propanediol. Examples of typical bio-route can include those described in U.S. Pat. No. 5,686,276, U.S. Pat. No. 5,633,362 and U.S. Pat. No. 5,821,092.

Copolymers of polytrimethylene ether diol or a blend of a high and a low molecular weight polytrimethylene ether diol can be used. Blends of the polytrimethylene ether diol and other cycloaliphatic hydroxyl containing either branched or linear oligomers can be used. Such hydroxyl containing oligomers are known to those skilled in the art. Examples of such hydroxyl containing oligomers can include those disclosed by Barsotti, et al. in U.S. Pat. No. 6,221,494.

The sag control agent can comprise one or more solvents. Any typical organic solvents can be used. Examples of solvents can include, but not limited to, aromatic hydrocarbons, such as, toluene, xylene; ketones, such as, acetone, methyl ethyl ketone, methyl isobutyl ketone, methyl amyl ketone and diisobutyl ketone; esters, such as, ethyl acetate, n-butyl acetate, t-butyl acetate, isobutyl acetate and a combination thereof.

In one example, the sag control agent comprises a reaction product of reactants consisting of said isocyanate component and said amine component. The isocyanate component can have any of the aforementioned isocyantes. The amine component can have any of the aforementioned fluorinated amines. In another example, the sag control agent comprises a reaction product of reactants consisting of hexamethylene diisocyanate and one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$ and a combination thereof. In yet another example, the sag control agent comprises a reaction product of reactants consisting of hexamethylenediisocyanate and one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$, and a combination thereof, and one or more of the polymers. In yet another example, the sag control agent comprises a reaction product of reactants consisting of hexamethylene diisocyanate and one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$ and a combination thereof, one or more solvents, and one or more of the polymers. In yet another example, the sag control agent comprises a reaction product of reactants consisting of hexamethylene diisocyanate and one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$ and a combination thereof, one or more of the aforementioned polymers, one or more aforementioned solvents, and the polytrimethylene ether diol. In yet another example, the sag control agent comprises a reaction product of reactants consisting of hexamethylene diisocyanate, one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$ and a combination thereof, and one or more of the aforementioned non-fluorinated amine. In yet another example, the sag control agent comprises a reaction product of reactants consisting of hexamethylene diisocyanate and one or more fluorinated amines selected from the group consisting of $C_6F_{13}C_2H_4-S-C_2H_4NH_2$, $C_6F_{13}C_2H_4-S(O)-C_2H_4NH_2$, $C_6F_{13}C_2H_4-S(O)_2-C_2H_4NH_2$, $CF_3(CF_2)_2O(CF_2)_2C_2H_4-S-C_2H_4NH_2$ and a combination thereof, and a hydroxyl acrylic polymer. In yet another example, the sag control agent consists of a reaction product of reactants consisting of hexamethylene diisocyanate and one or more fluorinated amines selected from the group consisting of $C_6F_{13}C_2H_4$—S—$C_2H_4NH_2$, $C_6F_{13}C_2H_4$—S(O)—$C_2H_4NH_2$, $C_6F_{13}C_2H_4$—S(O)$_2$—$C_2H_4NH_2$, $CF_3(CF_2)_2O(CF_2)_2C_2H_4$—S—$C_2H_4NH_2$ and a combination thereof, one or more solvents, and a hydroxyl acrylic polymer.

This invention is also directed to a coating composition. The coating composition can comprise: i) a sag control agent comprising a reaction product of reactants comprising an isocyanate component comprising an isocyanate and an amine component comprising a fluorinated amine; and ii) a polymer binder.

The fluorinated amine can have the formula:

Rf—X—NH$_2$  (I)

wherein, Rf is a fluorocarbon or perfluorocarbon having 1 to 20 carbon atoms, and X is a connecting di-radical $C_1$ to $C_{20}$ alkyl, $C_6$ to $C_{20}$ aryl, O—$R^1$—S(O)$_k$—$R^{1'}$, $R^1$—S(O)$_k$—$R^{1'}$, $R^1$—NR$^2$—$R^{1'}$, $C_1$ to $C_{20}$ substituted alkyl, $C_6$ to $C_{20}$ substituted aryl, or a combination thereof, k=0, 1 or 2; wherein $R^1$ or $R^{1'}$ is independently $C_1$ to $C_{10}$ alkyl, $C_6$ to $C_{10}$ aryl, $C_1$ to $C_{10}$ substituted alkyl, $C_6$ to $C_{10}$ substituted aryl, or a combination thereof, and wherein $R^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl.

The amine component can comprise any of the aforementioned fluorinated amines or a combination thereof. In addition to the fluorinated amine, the amine component can further comprise one or more of the aforementioned non-fluorinated amine, such as a non-fluorinated primary amine, a non-fluorinated secondary amine, or a combination thereof.

The isocyanate component can comprise any of the aforementioned isocyanates or a combination thereof.

The sag control agent can further comprise one or more of the aforementioned polymers.

The polymer binder of the coating composition can comprise any of the aforementioned polymers suitable for coating compositions and can be the same as or different from the polymers in the sag control agent. In one example, a sag control agent can be produced in the presence of one or more polymers the same as that of the binder polymers. The sag control agent can also be produced in the absence of polymers and added to a coating composition as described above.

The polymer binder can comprise a crosslinkable component and a crosslinking component. The crosslinkable component can comprise any of the aforementioned crosslinkable functional groups. In one example, the crosslinkable functional groups can be selected from hydroxyl, thiol, amino, amide, glycidyl, silane, carboxyl groups, and a combination thereof. The crosslinking component can comprise any of the aforementioned crosslinking functional groups that can react with the crosslinkable functional groups of the coating composition to form a coating. In one example, the crosslinking component can comprise one or more of the aforementioned isocyanates. In another example, the crosslinking component can comprise polyisocyanates, such as aliphatic polyisocyanates, cycloaliphatic polyisocyanates, aromatic polyisocyanates, isocyanate adducts, or a combination thereof. In yet another example, the crosslinking component can comprise thioisocyanate, acetoacetoxy, carboxyl, primary amine, secondary amine, epoxy, anhydride, ketimine, aldimine, orthoester, orthocarbonate, cyclic amide or a workable combination thereof.

In a further example, the coating composition can comprise: i) a sag control agent comprising a reaction product of reactants consisting of an isocyanate component and an amine component; and ii) a polymer binder.

In another example, the coating composition can comprise: i) a sag control agent comprising a reaction product of reactants consisting of hexamethylene diisocyanate and one or more fluorinated amines selected from the group consisting of $C_6F_{13}C_2H_4$—S—$C_2H_4NH_2$, $C_6F_{13}C_2H_4$—S(O)—$C_2H_4NH_2$, $C_6F_{13}C_2H_4$—S(O)$_2$—$C_2H_4NH_2$, $CF_3(CF_2)_2O(CF_2)_2C_2H_4$—S—$C_2H_4NH_2$ and a combination thereof; and ii) a polymer binder.

In yet another example, the coating composition can comprise: i) a sag control agent comprising a reaction product of reactants consisting of hexamethylene diisocyanate and one or more fluorinated amines selected from the group consisting of $C_6F_{13}C_2H_4$—S—$C_2H_4NH_2$, $C_6F_{13}C_2H_4$—S(O)—$C_2H_4NH_2$, $C_6F_{13}C_2H_4$—S(O)$_2$—$C_2H_4NH_2$, $CF_3(CF_2)_2O(CF_2)_2C_2H_4$—S—$C_2H_4NH_2$ and a combination thereof; and ii) a polymer binder comprising a hydroxyl acrylic polymer.

The coating composition can be used as a basecoat, a topcoat, or a clearcoat. It can also be used as a primer, a direct-to-metal topcoat, or a primerless topcoat.

The coating composition can be a solvent borne coating composition, a waterborne coating composition, a radiation curable coating composition, or a dual-cure coating composition that can be cured by two curing mechanisms such as radiation and chemical crosslink. The sag control agent of this disclosure can be produced in the absence of polymers and be added to any of the aforementioned coating compositions. The sag control agent can also be produced in the presence of one or more polymers, wherein said one or more polymers can be the same as or different from those for the aforementioned coating compositions.

In one example, the sag control agent is produced in the presence of a waterborne polymer binder. The sag control agent so produced can be mixed with other components to form the desired waterborne coating composition. In another example, the sag control agent is produced in the presence of a solvent borne polymer binder. The sag control agent so produced can be mixed with other components to form the desired solvent borne coating composition. In yet another example, the sag control agent is produced in the presence of a radiation polymer binder, such as a UV polymer binder. The sag control agent so produced can be mixed with other components to form the desired radiation curable coating composition, such as a UV curable coating composition. In yet another example, the sag control agent is produced in the presence of a dual-cure polymer binder. The sag, control agent so produced can be mixed with other components to form the desired dual-cure coating composition.

Typically, the coating composition can comprise in a range of from 0.1% to 20% of the reaction product of the reactants comprising the isocyanate component and the amine component, herein referred to as "the reaction product", weight percent of the total weight of the polymer binder of the coating composition. The coating composition can comprise in a range of from 0.1% to 20% of the reaction product in one example, 0.2% to 15% in another example, 0.2% to 10% in another example, 0.2% to 8% in yet another example, 0.2% to 5% in yet another example, weight percent of the total weight of the polymer binder. If the SCA to be used is produced in the absence of a polymer, such as the aforementioned SCA solution, polarity of solvent or solvent mix may need to be adjusted so the SCA can be dispersed into the coating without separation.

Typically, a catalyst can be used in the coating composition to reduce curing time and to allow curing of the coating composition at ambient temperatures. The ambient temperatures are typically referred to as temperatures in a range of from 18° C. to 35° C. Typical catalysts can include organic metal salts such as organotin compounds dibutyl tin dilaurate, dibutyl tin diacetate, dibutyl tin dichloride, dibutyl tin dibromide, zinc naphthenate; compounds containing tertiary amino groups, such as, triethylamine; triphenyl boron, tetraisopropyl titanate, triethanolamine titanate chelate, dibutyl tin dioxide, dibutyl tin dioctoate, tin octoate, aluminum titanate, aluminum chelates, zirconium chelate, hydrocarbon phosphonium halides, such as, ethyl triphenyl phosphonium iodide and other such phosphonium salts, and other catalysts or mixtures thereof known to those skilled in the art.

The coating composition can comprise one or more solvents. Typically, the coating composition can comprise 20% to 80% by weight, based on the weight of the coating composition, of one or more solvents. Typically, the coating composition of this disclosure can have a solid content in a range of from 20% to 80% by weight in one example, in a range of from 50% to 80% by weight in another example and in a range of from 60% to 80% by weight in yet another example, all based on the total weight of the coating composition. The coating composition of this disclosure can also be formulated at 100% solids by using a low molecular weight acrylic resin reactive diluent known to those skilled in the art.

Any typical organic solvents can be used to form the coating composition. Examples of solvents can include, but not limited to, aromatic hydrocarbons, such as, toluene, xylene; ketones, such as, acetone, methyl ethyl ketone, methyl isobutyl ketone, methyl amyl ketone and diisobutyl ketone; esters, such as, ethyl acetate, n-butyl acetate, isobutyl acetate and a combination thereof.

The coating composition can further comprise a pigment or a plurality of pigments. Typically, when the coating composition of this disclosure is utilized as a pigmented coating composition, it can contain a pigment or a plurality of pigments in a pigment to binder weight ratio of 1/100 to 350/100. The coating composition can be used as a basecoat or topcoat, such as a colored topcoat. Conventional inorganic and organic colored pigments, metallic flakes and powders, such as, aluminum flake and aluminum powders; special effects pigments, such as, coated mica flakes, coated aluminum flakes colored pigments, or a combination thereof can be used. Transparent pigments or pigments having the same refractive index as the cured binder can also be used. Such transparent pigments can be used in a pigment to binder weight ratio of 0.1/100 to 5/100. One example of such transparent pigment is silica.

The coating composition can also comprise coating additives. Examples of coating additives can include one or more ultraviolet light (UV) stabilizers, such as ultraviolet light absorbers, screeners, quenchers, and hindered amine light stabilizers; one or more antioxidants; wetting agents, leveling and flow control agents, rheological control agents, such as highly disperse silica, or fumed silica; thickeners, such as partially crosslinked polycarboxylic acid or polyurethanes; and antifoaming agents. The additives can be used in conventional amounts familiar to those skilled in the art.

Examples of the UV stabilizers can include hydroxyphenyl benzotriazoles, such as, 2-(2-hydroxy-5-methylphenyl)-2H-benzotrazole, 2-(2-hydroxy-3,5-di-tert.amyl-phenyl)-2H-benzotriazole, 2[2-hydroxy-3,5-di(1,1-dimethylbenzyl)phenyl]-2H-benzotriazole, reaction product of 2-(2-hydroxy-3-tert.butyl-5-methyl propionate)-2H-benzotriazole and polyethylene ether glycol having a weight average molecular weight of 300, 2-(2-hydroxy-3-tert.butyl-5-iso-octyl propionate)-2H-benzotriazole; hydroxyphenyl s-triazines, such as, 2-[4((2,-hydroxy-3-dodecyloxy/tridecyloxypropyl)-oxy)-2-hydroxyphenyl]-4,6-bis(2,4-dimethylphenyl)-1,3,5-triazine, 2-[4(2-hydroxy-3-(2-ethylhexyl)-oxy)-2-hydroxyphenyl]-4,6-bis(2,4-dimethylphenyl)1,3,5-triazine, 2-(4-octyloxy-2-hydroxyphenyl)-4,6-bis(2,4-dimethylphenyl)-1,3,5-triazine; hydroxybenzophenone UV absorbers, such as, 2,4-dihydroxybenzophenone, 2-hydroxy-4-octyloxybenzophenone, and 2-hydroxy-4-dodecyloxybenzophenone.

Examples of hindered amine light stabilizers can include N-(1,2,2,6,6-pentamethyl-4-piperidinyl)-2-dodecyl succinimide, N(1acetyl-2,2,6,6-tetramethyl-4-piperidinyl)-2-dodecyl succinimide, N-(2hydroxyethyl)-2,6,6,6-tetramethylpiperidine-4-ol-succinic acid copolymer, 1,3,5 triazine-2,4,6-triamine, N,N'''-[1,2-ethanediybis[[[4,6-bis[butyl(1,2,2,6,6-pentamethyl-4-piperidinyl)amino]-1,3,5-triazine-2-yl]imino]-3,1-propanediyl]]bis[N,N'''-dibutyl-N',N'''-bis(1,2,2,6,6-pentamethyl-4-piperidinyl)], poly-[[6-[1,1,3,3-tetramethylbutyl)-amino]-1,3,5-trianzine-2,4-diyl][2,2,6,6-tetramethylpiperidinyl)-imino]-1,6-hexane-diyl[(2,2,6,6-tetramethyl-4-piperidinyl)-imino]), bis(2,2,6,6-tetramethyl-4-piperidinyl)sebacate, bis(1,2,2,6,6-pentamethyl-4-piperidinyl)sebacate, bis(1-octyloxy-2,2,6,6-tetramethyl-4-piperidinyl)sebacate, bis(1,2,2,6,6-pentamethyl-4-piperidinyl)[3,5bis(1,1-dimethylethyl-4-hydroxy-phenyl) methyl]butyl propanedioate, 8-acetyl-3-dodecyl-7,7,9,9,-tetramethyl-1,3,8-triazaspiro(4,5)decane-2,4-dione, and dodecyl/tetradecyl-3-(2,2,4,4-tetramethyl-2I-oxo-7-oxa-3,20-diazal dispiro(5.1.11.2)henicosan-20-yl)propionate.

Examples of antioxidants can include tetrakis[methylene (3,5-di-tert-butylhydroxy hydrocinnamate)]methane, octadecyl 3,5-di-tert-butyl-4-hydroxyhydrocinnamate, tris(2,4-di-tert-butylphenyl)phosphite, 1,3,5-tris(3,5-di-tert-butyl-4-hydroxybenzyl-1,3,5-triazine-2,4,6(1H,3H,5H)-trione and benzenepropanoic acid, 3,5-bis(1,1-dimethyl-ethyl)-4-hydroxy-C7-C9 branched alkyl esters. Typically, useful antioxidants can also include hydroperoxide decomposers, such as, 9,10-dihydro-9-oxa-10-phosphenanthrene-10-oxide, triphenyl phosphate and other organo-phosphorous compounds, some of which can be commercially available.

Examples of wetting agents, leveling and flow control agents can include: Resiflow®S (polybutylacrylate) from Estron Chemical, Inc, BYK® 320 and 325 (high molecular weight polyacrylates) and BYK® 347 (polyether-modified siloxane) from Byk-Chemie, under respective registered trademarks.

Depending upon the type of crosslinking groups, the coating composition can be formulated as one-pack (1K) or two-pack (2K) coating composition. If, for example, polyisocyanates with free isocyanate groups are used in the crosslinking component, the coating composition can be formulated as a two-pack coating composition in that the crosslinking component is mixed with other components of the coating composition only shortly before coating application. If blocked polyisocyanates are, for example, used as the crosslinking groups, the coating compositions can be formulated as a one-pack (1K) coating composition. The coating composition can be further adjusted to spray viscosity with organic solvents as determined by those skilled in the art before being applied. One-pack coating composition can also include, for example, a UV curable coating composition.

In a typical two-pack coating composition comprising two packages, the two packages are mixed together shortly before application. In one example, a first package can contain the crosslinkable component having one or more crosslinkable functional groups, and the sag control agent of this disclosure. Optionally, one or more pigments can be dispersed in the first package using conventional dispersing techniques, for example, ball milling, sand milling, and attritor grinding. The second package can contain a crosslinking component having crosslinking functional groups.

This disclosure is further directed to a process for forming a sag-free coating layer on a substrate. The process can comprise the steps of:

A) applying a coating composition over said substrate forming a sag-free wet coating layer having a wet coating thickness in a range Of from 8 to 36 mils, wherein said coating composition comprises:
   i) a sag control agent comprising a reaction product of reactants comprising an isocyanate component comprising an isocyanate and an amine component comprising a fluorinated amine having the formula:

wherein, Rf is a fluorocarbon or perfluorocarbon having 1 to 20 carbon atoms, and X is a connecting di-radical $C_1$ to $C_{20}$ alkyl, $C_6$ to $C_{20}$ aryl, O—$R^1$—S(O)$_k$—$R^{1'}$, $R^1$—S(O)$_k$—$R^{1'}$, $R^1$—$NR^2$—$R^{1'}$, $C_1$ to $C_{20}$ substituted alkyl, $C_6$ to $C_{20}$ substituted aryl, or a combination thereof, k=0, 1 or 2; wherein $R^1$ or $R^{1'}$ is independently $C_1$ to $C_{10}$ alkyl, $C_6$ to $C_{10}$ aryl, $C_1$ to $C_{10}$ substituted alkyl, $C_5$ to $C_{10}$ substituted aryl, or a combination thereof, and wherein $R^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl; and
   ii) a polymer binder; and
B) curing said sag-free wet coating layer to form said sag-free coating layer.

Any of the aforementioned coating compositions of this invention can be suitable for the process.

The coating composition according to the disclosure can be suitable for vehicle and industrial coatings. In the context of vehicle coating, the coating composition can be used both for vehicle original equipment manufacturing (OEM) coatings and for repairing or refinishing coatings of vehicles and vehicle parts. Curing of the coating composition can be accomplished at ambient temperatures, such as temperatures in a range of from 15° C. to 35° C., or at elevated temperatures, such as at temperatures in a range of from 35° C. to 150° C. Typical curing temperatures in a range of from 15° C. to 80° C. can be used for vehicle repairs or refinish coatings. In one example, curing can be done at a temperature in a range of from 15° C. to 60° C. In another example, curing can be done at a temperature in a range of from 15° C. to 50° C.

In a further example, the process can consist of the steps of: A) applying a coating composition over said substrate forming a sag-free wet coating layer having a wet coating thickness in a range of from 8 to 36 mils, wherein said coating composition comprises the sag control agent comprising a reaction product of reactants comprising the isocyanate component, the amine component comprising the fluorinated amine, and the polymer binder, and B) curing said sag-free wet coating layer to form said sag-free coating layer.

In an even further example, the process can consist of the steps of: A) applying a coating composition over said substrate forming a sag-free wet coating layer having a wet coating thickness in a range of from 8 to 36 mils, wherein said coating composition comprises the sag control agent comprising a reaction product of reactants consisting of the isocyanate component, the amine component consisting of the fluorinated amine, and the polymer binder; and B) curing said sag-free wet coating layer to form said sag-free coating layer.

The coating composition can be applied by conventional techniques, such as, spraying, electrostatic spraying, dipping, brushing, and flow coating. Typically, the coating can be applied to a substrate to form a sag-free coating layer having a wet coating thickness, also known as wet film thickness (wft), in a range of, in one example from 8 to 36 mils (about 203 to 914 microns), in another example from 10 to 36 mils (about 254 to 914 microns), in yet another example from 12 to 36 mils (about 305 to 914 microns), in yet another example from 14 to 36 mils (about 356 to 914 microns), and in yet further example from 16 to 36 mils (about 406 to 914 microns). After curing and drying, the sag-free coating layer can have a dry coating thickness in a range of from 2 to 20 mils in one example, 4 to 20 mils in another example, 6 to 20 mils in yet another example, and 8 to 20 mils in further another example.

Conventional sag control agents that are reaction products of non-fluorinated primary amines and isocyanates are so called "opaque" sag control agents due to their opalescent appearance in coatings (Fred G. H. van Wijk, page 2-5, 12, 2007, European Coatings Journal). In addition, these conventional sag control agents have limited effect on improving gloss or DOI of coatings.

The Applicants unexpectedly discovered that the SCAs of this invention that are reaction products of fluorinated amine have clear appearance suitable for the use in clearcoats. The Applicants further discovered unexpectedly that the SCAs of this invention have greater effect on improving gloss or DOI of coatings comparing to the conventional SCAs that are from non-fluorinated amines.

This disclosure is further directed to a coated article comprising a substrate and at least one sag-free coating layer over said substrate formed from the coating composition of this disclosure. The sag-free coating layer can have a dry coating thickness in a range of from 4 to 20 mils.

A substrate suitable for this disclosure can be a treated metal, bare metal such as blasted steel, aluminum or other metal or alloys; plastic or other polymer or resinous materials; concrete; wood; or other natural or manmade materials. A substrate can also be a vehicle, vehicle body, or vehicle body parts. In one example, the substrate can be a vehicle, vehicle body, or vehicle body parts.

The coated article can also be a piece of furniture; household appliances, such as a refrigerator, a dishwasher, a washer and dryer, or an air conditioner; electronic appliances, such as a computer, a TV set, a video player, a DVD player, a cell phone, or a radio set; sports equipments, such as an exercise bike, a bicycle, a treadmill, a pool table, a basketball net set, a glider, or a water jet; or any other articles that are coated or can be coated with one or more coatings.

Testing Procedures

Dry Film Thickness—can be measured according to the test method ASTM D4138.

Viscosity—can be measured using (1) Zahn Viscosity as determined using a #1 Zahn cup according to ASTM D 1084 Method D; (2) Gardner-Holdt Letter scale according to ASTM D1545; or (3) Brookfield viscometer; as specified.

Orange Peel can be tested using Wavescan DOI method from BYK Gardner, Columbia, Md., USA, with lower number representing smoother paint having less orange peels and higher number representing paint having more orange peels.

Sag measurement—Sagging of coatings can be measured according to ASTM D 4400 using a multinotch applicator. In brief, a coating composition is applied to a panel to form coating stripes at different thickness using the multinotch applicator. The panel is then positioned vertically with the coating stripes across the panel horizontally. Each stripe is visually examined for sagging. Film thickness of the thickest coating stripe that is sag free is recorded in mils (1 mil equals to about 0.0254 mm). Wet film thickness (wft), also referred to as wet coating thickness, can be determined based on indications of the multinotch applicator used for the coating or with other instruments or methods known to those skilled in the art. Examples of commercially available instruments can include wet film thickness measuring wheels or combs.

Gloss—can be measured with standard test method for specular gloss according to ASTM D 523.

In the following examples, all parts and percentages are on a weight (herein referred to as "wt") basis unless otherwise indicated. "Mw" weight average molecular weight and "Mn" means number average molecular weight.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Procedure 1

Preparation of Hydroxyl Acrylic Polymer

The hydroxyl acrylic polymers were formed by free-radical copolymerization using conventional processes well known to those skilled in the art with the following weight parts: 13.7 parts t-butylacetate, 14.6 parts methyl methacrylate, 5.9 parts styrene, 11.7 parts hydroxyethyl methacrylate, 14.6 parts n-butyl acrylate, 11.7 parts 2-ethylhexyl methacrylate, and 1.2 parts t-butylacetate. An initiator mixture of 3.4 parts azobisnitrile (available as Vazo® 67 from E. I. DuPont de Nemours and Company, Wilmington, Del., USA, and under respective registered trademark) and 23.2 parts t-butylacetate was used.

Procedure 2

Synthesis of Comparative Sag Control Agent

Benzyl amine (available from BASF, Florham Park, N.J.) 1.7% by weight (wt) was mixed with 1.34% by wt of 1,6 Hexamethylene Diisocyanate, in the presence of 96.36% by wt of the hydroxyl acrylic polymer from Procedure 1. The reaction was stirred for 5 minutes. Final product contains 3% (weight percent) of the reaction product of the reactants Benzyl amine and 1,6 Hexamethylene Diisocyanate in the hydroxyl acrylic polymer.

Procedure 3

Synthesis of Fluorinated Sag Control Agent

Following ingredients were mixed according to Table 1. Fluorinated amine was added to the acrylic polymer while mixing during a 10 minute time period. Continued to mix on a vortex for 10 minutes while adding 1,6-Hexamethylene Diisocyanate. Final product contains 3% (weight percent) of the reaction product of the reactants fluorinated amine and 1,6-Hexamethylene Diisocyanate in the hydroxyl acrylic polymer.

TABLE 1

| Ingredients. | | |
|---|---|---|
| | Wt % | Weight (gram) |
| Hydroxyl acrylic polymer from Procedure 1 | 92.46 | 832.11 |
| Fluorinated Amine [1] | 5.68 | 51.14 |
| Solvent [2] | 0.29 | 2.59 |
| 1,6-Hexamethylene Diisocyanate [3] | 1.29 | 11.57 |
| Solvent [2] | 0.29 | 2.59 |
| Total | 100 | 900 |

[1] Fluorinated amine was $C_6F_{13}C_2H_4$—S—$C_2H_4NH_2$ as described in U.S. Pat. application. 2009/0,143,608.
[2] The solvent used was t-butyl acetate.
[3] 1,6-Hexamethylene Diisocyanate was Desmodur H available from Bayer MaterialScience, Pittsburg, PA, USA.

Coating Composition and Property

Coating compositions were prepared according to Table 2. Comparative 1 (Comp 1) contained no sag control agent. Comparative 2 (Comp 2) contained conventional non-fluorinated SCA. Example 1 contained the fluorinated SCA of this disclosure.

TABLE 2

| Coating Composition. | | | |
|---|---|---|---|
| | Comp 1 (NO SCA) (Grams) | Comp 2 (Conventional SCA) (Grams) | Example 1 (Grams) |
| Hydroxyl acrylic polymer from Procedure 1 | 70 | 60 | 60 |
| UV Stabilizer [4] | 1.5 | 1.5 | 1.5 |
| UV Absorber [4] | 1.5 | 1.5 | 1.5 |
| Polyether modified polydimethylsiloxane [5] | 0.2 | 0.2 | 0.2 |
| 2-ethylhexylacetate | 9.3 | 9.3 | 9.3 |
| Hydroxy oligomer [6] | 18.2 | 18.2 | 18.2 |
| Organotin compound [7] | 1.4 | 1.4 | 1.4 |
| t-butyl acetate | 8.5 | 8.5 | 8.5 |
| Aluminum pigment paste 1 [8] | 1.3 | 1.3 | 1.3 |
| Aluminum pigment paste 2 [9] | 1.7 | 1.7 | 1.7 |
| Comparative non-fluorinated SCA from Procedure 2 | 0 | 10 | 0 |
| Fluorinated SCA from Procedure 3 | 0 | 0 | 10 |
| Isocyanate Activator [10] | 25 | 25 | 25 |

[4] UV Stabilizer was liquid hindered amine light stabilizer available as Tinuvin ® 292. UV Absorber used was a mixture of hydroxyphenyl class compounds, available as Tinuvin ® 1130. Both are available from Ciba Specialty Chemicals Corporation, Tarrytown, New York, under respective registered trademarks.
[5] Polyether modified polydimethylsiloxane used was BYK ®-333, available from BYK Chemie, Wesel, Germany, under respective registered trademark.
[6] Hydroxy oligomer was a reaction product of 3 moles of caprolactone and 1 mole of 1,4-cyclohexane dimethanol, as described in U.S. Pat. No. 6,875,514.
[7] Organotin compound was organotin (2.0%) in pentanedione (98.0%), available as VG805 ™ from DuPont, Wilmington, DE, USA, under respective trademark.
[8] Aluminum pigment paste 1 was a medium particle size, regular purity, non-leafing aluminum pigment, available as Sparkle Silver ® 3641 from Silberline ® Manufacturing Company, Inc, Tamaqua, PA, USA, under respective registered trademark.
[9] Aluminum pigment paste 2 was aluminum flakes available as STAPA ® MOBILUX 33313, from Eckart, Painesville, OH, USA, under respective registered trademark.
[10] Isocyanate Activator was aliphatic polyisocyanate, available as 9T00-A ™ from DuPont, Wilmington, DE, USA, under respective trademark.

Each of the coating compositions of Table 2 was applied on individual 4×12" blasted steel panels available from East Coast Steel Incorporated, Salina Rd, Sewell, N.J., USA, using wet draw down forming a wet coating layer at various desired thicknesses. The maximum thickness without sagging was recorded as sag thickness (mil) for each of the coating compositions. DOI, gloss and orange peel were measured according to Testing Procedures. Coating properties are shown in Table 3. Coatings with the fluorinated SCA had improved DOI and orange peel, and also had improved gloss at both 20° and 60°.

TABLE 3

Coating Properties.

|  | Comp 1 | Comp 2 | Example 1 |
|---|---|---|---|
| Wavescan DOI [11] | 53 | 65 | 75 |
| Orange Peel [12] | 44 | 38 | 30 |
| Gloss at 20° [13] | 60 | 65 | 70 |
| Gloss at 60° [13] | 80 | 85 | 92 |
| Sag thickness (mils) [14] (Dry coating thickness) | 3 (0.07 mm) | 8 (0.20 mm) | 8 (0.20 mm) |
| Sag thickness (mils) [14] (Wet coating thickness) | 6 (0.15 mm) | 16 (0.40 mm) | 16 (0.40 mm) |

[11] DOI was measured by Wavescan DOI according to Byk Gardner Columbia, MD, USA.
[12] Orange Peel was measured by Wavescan DOI, according to BYK Gardner, Columbia, MD, USA.
[13] Gloss readings at 20° and 60° were measured using Glossmeter, available from BYK Gardner, Columbia, MD, USA.
[14] Sag thickness was the maximum dry coating thickness without sagging. Units shown are in mils. Approximate thicknesses in millimeters (mm) based on the mil units are also shown in parentheses.

Coating compositions for Comparative 3 (No SCA), Comparative 4 (conventional non-fluorinated SCA) and Example 2 (Fluorinated SCA) were prepared according to Table 4. Coating properties are shown in Table 5. Coatings having conventional non-fluorinated SCA showed haze and had microfoam formation. The coating having the fluorinated SCA was clear and without microfoam formation.

TABLE 4

Coating Compositions.

|  | Comp 3 (wt) | Comp 4 (wt) | Example 2 (wt) |
|---|---|---|---|
| Hydroxyl acrylic polymer from Procedure 1 | 110 | 30 | 30 |
| Comparative SCA from Procedure 2 | — | 80 | — |
| Fluorinated SCA from Procedure 3 | — | — | 80 |
| Solvent 1 [15] | 20 | 20 | 20 |
| Solvent 2 [16] | 20 | 20 | 20 |
| 2-ethylhexylacetate | 2 | 2 | 2 |
| Isocyanate Activator [17] | 18.88 | 18.88 | 18.88 |
| Total | 170.88 | 170.88 | 170.88 |

[15] Solvent 1 was Parachlorobenzotrifluoride, available as OXSOL ® 100 from MANA, New York, NY, USA under respective registered trademark.
[16] Solvent 2 was a liquid solvent containing aromatic hydrocarbons, available as Aromatic 100 Fluid from Exxon Mobil Chemical, Houston, TX, USA.
[17] Isocyanate Activator was aliphatic polyisocyanate (HDI trimer) available as Desmodur ® N3300 from Bayer MaterialScience AG, Leverkusen, Germany, under respective registered trademark.

TABLE 5

Coating Property.

|  | Comp 3 | Comp 4 | Example 2 |
|---|---|---|---|
| Haze [18] | 98 | 124 | 100 |
| Appearance [19] | No microfoam | Microfoam observed | No microfoam |

[18] Haze was measured using Hazemeter, available from BYK Gardner, Columbia, MD, USA, on the coated panels. Lower number indicates less hazy.
[19] Appearance assessment was done by visual inspection.

What is claimed is:

1. A sag control agent comprising a reaction product of reactants comprising an isocyanate component comprising an isocyanate and an amine component comprising a fluorinated amine, wherein said fluorinated amine has the formula:

Rf—X—NH$_2$     (I)

wherein, Rf is a fluorocarbon or perfluorocarbon having 1 to 20 carbon atoms, and X is a connecting di radical C$_6$ to C$_{20}$ aryl, O—R$^1$—S(O)$_k$—R$^{1'}$, R$^1$—S(O)$_k$—R$^{1'}$, R$^1$—NR$^2$—R$^{1'}$, C$_1$ to C$_{20}$ substituted alkyl wherein one or more hydrogen atoms are substituted with a C$_1$ to C$_{10}$ alkyl or C$_1$ to C$_{10}$ substituted alkyl, C$_6$ to C$_{20}$ substituted aryl wherein one or more hydrogen atoms are substituted with a C$_1$ to C$_{10}$ alkyl or C$_1$ to C$_{10}$ substituted alkyl, or a combination thereof, k=0, 1 or 2; wherein R$^1$ or R$^{1'}$ is independently C$_1$ to C$_{10}$ alkyl, C$_6$ to C$_{10}$ aryl, C$_1$ to C$_{10}$ substituted alkyl, C$_6$ to C$_{10}$ substituted aryl, or a combination thereof, and wherein R$^2$ is H, C$_1$ to C$_{10}$ alkyl, C$_6$ to C$_{10}$ aryl, C$_1$ to C$_{10}$ substituted alkyl, or C$_6$ to C$_{10}$ substituted aryl.

2. The sag control agent of claim 1 further comprising a pigment.

3. The sag control agent of claim 1, wherein X is a connecting di-radical O(CH$_2$)$_m$—S(O)$_k$—(CH$_2$)$_n$, (CH$_2$)$_m$—S(O)$_k$—(CH$_2$)$_n$, (CH$_2$)$_m$—NR$^2$—(CH$_2$)$_n$, substituted (CH$_2$)$_m$ wherein one or more hydrogen atoms are substituted with a C$_1$ to C$_{10}$ alkyl or C$_1$ to C$_{10}$ substituted alkyl, O(CH$_2$)$_m$—S(O)$_k$—(CH$_2$)$_n$, (CH$_2$)$_m$—S(O)$_k$—(CH$_2$)$_n$, or (CH$_2$)$_m$—NR$^2$—(CH$_2$)$_n$, wherein m and n are independently zero or positive integers, and m+n is in a range of from 3 to 20.

4. The sag control agent of claim 3, wherein m+n is in a range of from 3 to 6.

5. The sag control agent of claim 1, wherein said fluorocarbon or said perfluorocarbon has 1 to 8 carbon atoms.

6. The sag control agent of claim 1, wherein said amine component comprises one or more fluorinated amines selected from the group consisting of C$_6$F$_{13}$C$_2$H$_4$—S—C$_2$H$_4$NH$_2$, C$_6$F$_{13}$C$_2$H$_4$—S(O)—C$_2$H$_4$NH$_2$, C$_6$F$_{13}$C$_2$H$_4$—S(O)$_2$—C$_2$H$_4$NH$_2$, CF$_3$(CF$_2$)$_2$O(CF$_2$)$_2$C$_2$H$_4$—S—C$_2$H$_4$NH$_2$, and a combination thereof.

7. The sag control agent of claim 1, wherein said isocyanate is a monoisocyanate, a diisocyanate, a trimer of diisocyanate, a polyisocyanate, or a combination thereof.

8. The sag control agent of claim 1, wherein said isocyanate is hexamethylene diisocyanate.

9. The sag control agent of claim 1 further comprising one or more polymers.

10. The sag control agent of claim 9, wherein said one or more polymers are one or more acrylic polymers, one or more polyester polymers, one or more polyether polymers, or a combination thereof.

11. The sag control agent of claim 10, wherein said one or more acrylic polymers comprise a hydroxyl acrylic polymer.

12. The sag control agent of claim 10, wherein said one or more polyether polymers comprise a polytrimethylene ether diol having a Mn (number average molecular weight) in a range of from 500 to 10,000.

13. The sag control agent of claim 12, wherein said polytrimethylene ether diol is polymerized from bio-derived 1,3-propanediol.

14. The sag control agent of claim 1 further comprising one or more solvents.

15. The sag control agent of claim 1, wherein said sag control agent comprises a reaction product of reactants consisting of said isocyanate component and said amine component.

16. The sag control agent of claim 1, wherein said sag control agent comprises a reaction product of reactants consisting of hexamethylene diisocyanate and one or more fluorinated amines selected from the group consisting of C$_6$F$_{13}$C$_2$H$_4$—S—C$_2$H$_4$NH$_2$, C$_6$F$_{13}$C$_2$H$_4$—S(O)—C$_2$H$_4$NH$_2$, C$_6$F$_{13}$C$_2$H$_4$—S(O)$_2$—C$_2$H$_4$NH$_2$, CF$_3$(CF$_2$)$_2$O(CF$_2$)$_2$C$_2$H$_4$—S—C$_2$H$_4$NH$_2$, and a combination thereof.

17. The sag control agent of claim 1, wherein said amine component further comprises a non-fluorinated primary amine, a non-fluorinated secondary amine, or a combination thereof.

18. The sag control agent of claim 1, wherein said amine component comprises 50% to 100%, weight percent of the total weight of the amine component, of said fluorinated amine.

19. The sag control agent of claim 1 further comprising a polymer binder of a coating composition, wherein the polymer binder comprises a crosslinkable component and a crosslinking component.

20. A process for forming a sag-free coating layer on a substrate, said process comprising the steps of:
  A) applying a coating composition over said substrate forming a sag-free wet coating layer having a wet coating thickness in a range of from 8 to 36 mils, wherein said coating composition comprises:
  i) a sag control agent comprising a reaction product of reactants comprising an isocyanate component comprising an isocyanate and an amine component comprising a fluorinated amine having the formula:

Rf—X—NH$_2$ (I)

wherein, Rf is a fluorocarbon or perfluorocarbon having 1 to 20 carbon atoms, and X is a connecting di-radical, $C_6$ to $C_{20}$ aryl, O—R$^1$—S(O)$_k$—R$^{1'}$, R$^1$—S(O)$_k$—R$^{1'}$, R$^1$—NR$^2$—R$^{1'}$, $C_1$ to $C_{20}$ substituted alkyl wherein one or more hydrogen atoms are substituted with a $C_1$ to $C_{10}$ alkyl or $C_1$ to $C_{10}$ substituted alkyl, $C_6$ to $C_{20}$ substituted aryl wherein one or more hydrogen atoms are substituted with a $C_1$ to $C_{10}$ alkyl or $C_1$ to $C_{10}$ substituted alkyl, or a combination thereof, k=0, 1 or 2; wherein R$^1$ or R$^{1'}$ is independently $C_1$ to $C_{10}$ alkyl, $C_6$ to $C_{10}$ aryl, $C_1$ to $C_{10}$ substituted alkyl, $C_6$ to $C^{10}$ substituted aryl, or a combination thereof, and wherein R$^2$ is H, $C_1$ to $C_{10}$ alkyl, $C_6$ to $C_{10}$ aryl, $C_1$ to $C_{10}$ substituted alkyl, or $C_6$ to $C_{10}$ substituted aryl; and
  ii) a polymer binder; and
  B) curing said sag-free wet coating layer to form said sag-free coating layer.

21. The process of claim 20, wherein said step B) is performed at a temperature in a range of from 15° C. to 50° C.

22. The process of claim 20, wherein said sag-free wet coating layer has a wet coating thickness in a range of from 10 to 36 mils.

23. The process of claim 20, wherein said sag-free coating layer has a dry coating thickness in a range of from 4 to 20 mils.

* * * * *